US012678402B2

(12) United States Patent
Temtsin-Krayz et al.

(10) Patent No.: US 12,678,402 B2
(45) Date of Patent: *Jul. 14, 2026

(54) TREATMENT WITH POWDERED INTRANASAL EPINEPHRINE

(71) Applicant: Nasus Pharma Ltd., Tel Aviv (IL)

(72) Inventors: Galia Temtsin-Krayz, Ashdod (IL); Pavel Kazhdan, Yavne (IL)

(73) Assignee: Nasus Pharma Ltd., Tel Aviv (IL)

( * ) Notice: Subject to any disclaimer, the term of this patent is extended or adjusted under 35 U.S.C. 154(b) by 532 days.

This patent is subject to a terminal disclaimer.

(21) Appl. No.: 17/911,523

(22) PCT Filed: Mar. 16, 2021

(86) PCT No.: PCT/IL2021/050288
§ 371 (c)(1),
(2) Date: Sep. 14, 2022

(87) PCT Pub. No.: WO2021/186437
PCT Pub. Date: Sep. 23, 2021

(65) Prior Publication Data
US 2023/0105615 A1    Apr. 6, 2023

Related U.S. Application Data

(63) Continuation of application No. 17/135,528, filed on Dec. 28, 2020, now Pat. No. 11,400,045.

(60) Provisional application No. 62/989,913, filed on Mar. 16, 2020.

(51) Int. Cl.
*A61K 31/137* (2006.01)
*A61K 9/00* (2006.01)
*A61K 9/14* (2006.01)
*A61K 9/16* (2006.01)
*A61P 43/00* (2006.01)

(52) U.S. Cl.
CPC ............ *A61K 9/0043* (2013.01); *A61K 9/143* (2013.01); *A61K 9/145* (2013.01); *A61K 9/1623* (2013.01); *A61K 31/137* (2013.01)

(58) Field of Classification Search
CPC ...... A61K 9/0043; A61K 9/143; A61K 9/145; A61K 9/1623; A61K 31/137; A61K 9/1611; A61P 43/00; A61P 37/08
See application file for complete search history.

(56) References Cited

U.S. PATENT DOCUMENTS

| | | |
|---|---|---|
| 6,462,090 B1 | 10/2002 | Slutsky et al. |
| 6,866,039 B1 | 3/2005 | Wright et al. |
| 6,945,953 B2 | 9/2005 | Wright |
| 8,673,360 B2 | 3/2014 | Nagata et al. |
| 8,875,704 B2 | 11/2014 | Djupesland et al. |
| 9,211,253 B2 | 12/2015 | Crystal et al. |
| 9,556,260 B2 | 1/2017 | Frey, II et al. |
| 11,116,723 B2 * | 9/2021 | Temtsin-Krayz .... A61K 9/1682 |
| 11,202,757 B2 * | 12/2021 | Temtsin-Krayz .... A61K 31/485 |
| 11,400,045 B2 * | 8/2022 | Temtsin-Krayz ....... A61P 43/00 |
| 11,844,859 B2 * | 12/2023 | Temtsin-Krayz .... A61K 31/485 |
| 2001/0049391 A1 | 12/2001 | Alfonso et al. |
| 2003/0178440 A1 | 9/2003 | Wright |
| 2005/0028813 A1 | 2/2005 | Harrison |
| 2007/0119451 A1 | 5/2007 | Wang et al. |
| 2007/0178166 A1 | 8/2007 | Bernstein et al. |
| 2008/0292713 A1 | 11/2008 | Seville et al. |
| 2009/0041800 A1 | 2/2009 | Woiwode et al. |
| 2009/0246281 A1 | 10/2009 | Goller et al. |
| 2010/0178331 A1 | 7/2010 | Nagata et al. |
| 2011/0033544 A1 | 2/2011 | Nagata et al. |
| 2012/0145150 A1 | 6/2012 | Donovan et al. |
| 2014/0073562 A1 | 3/2014 | Djupesland |
| 2015/0005356 A1 | 1/2015 | Fleming |
| 2015/0010633 A1 | 1/2015 | Li et al. |
| 2016/0220489 A1 | 8/2016 | Fleming et al. |
| 2016/0243060 A1 | 8/2016 | Standley et al. |
| 2016/0354288 A1 | 12/2016 | Uehara et al. |
| 2020/0069582 A1 | 3/2020 | Rubin |

FOREIGN PATENT DOCUMENTS

| | | |
|---|---|---|
| CA | 3030359 A1 | 2/2018 |
| CN | 102166219 A | 8/2011 |
| CN | 110505873 A | 11/2019 |
| EP | 0588255 A1 | 3/1994 |
| EP | 2648788 A1 | 10/2013 |
| JP | 2018533911 A | 11/2018 |
| JP | 2019527703 A | 10/2019 |
| WO | 2009050726 A2 | 4/2009 |
| WO | 2015034822 A1 | 3/2015 |
| WO | 2016133863 A1 | 8/2016 |
| WO | 2019/038756 A1 | 2/2019 |
| WO | 2019163520 A1 | 8/2019 |

OTHER PUBLICATIONS

Reber, L. L., Hernandez, J. D., Galli, S. J., "The pathophysiology of anaphylaxis", J Allergy Clin Immunol. 2017; 140(2), pp. 335-348.
Turner, P. J., Jerschow, E., Umasunthar, T., Lin, R., Campbell, D. E. and Boyle, R. J., "Fatal Anaphylaxis: Mortality Rate and Risk Factors", J Allergy Clin Immunol. Pract, 2017; 5(5), pp. 1169-1178.
Kemp, S. F., Lockey, R. F., Simons, F. E. and World Allergy Organization ad hoc Committee on Epinephrine in Anaphylaxis, "Epinephrine: the drug of choice for anaphylaxis—a statement of the world allergy organization", World Allergy Organization Journal, 2008; 1(7 Suppl), pp. S18-S26.
Sicherer, S. H. and Simons, F. E. R., "Epinephrine for First-aid Management of Anaphylaxis", American Academy of Pediatrics. Mar. 2017; 139(3), 11 pages.

(Continued)

*Primary Examiner* — Mina Haghighatian
(74) *Attorney, Agent, or Firm* — Banner & Witcoff, Ltd.

(57) ABSTRACT

Disclosed is a pharmaceutical composition in dry powder form for intranasal administration, comprising an anti-anaphylactic adrenergic receptor agonist in the form of dry powder for intranasal administration, the composition comprising solid particles of the active agent in combination with at least one functional additive, and solid particles of an inert carrier.

13 Claims, 4 Drawing Sheets

(56) References Cited

OTHER PUBLICATIONS

Ring, J., Beyer, K., Biedermann, T., Bircher, A., Duda, D., Fischer J., et al., "Guideline for acute therapy and management of anaphylaxis", Allergo Journal Int. 2014; 23(3), pp. 96-112.

Mylan Inc., "Highlights of Prescribing Information. EPIPEN® (epinephrine injection, USP)", USA: FDA; Revised: Aug. 2018, https://www.accessdata.fda.gov/scripts/cder/daf/. Accessed [Aug. 6, 2019].

Gold, M.S., Sainsbury, R., "First aid anaphylaxis management in children who were prescribed an epinephrine autoinjector device (EpiPen)", J Allergy Clin Immunol., Jul. 2000; vol. 106, No. 1, Part 1, pp. 171-176.

Chen, J., Chilampalli, C., Decastro, G., Narayanan, E., Wakaskar, R., Atiee, G. J., "An Open-Label, 5-Treatment, Crossover, Single-Dose Pharmacokinetic Study of Epinephrine Nasal Spray in Comparison to EpiPen® Intramuscular Injection in Healthy Adults With Seasonal Allergies (abstract 434)", AAAAI Annual Meeting. San Francisco, CA, USA, INSYS Development Company, Inc. 2019.

Cady, R. K, Mcallister, P. J., Spierings, E. L., et al., "A randomized, double-blind, placebo-controlled study of breath powered nasal delivery of sumatriptan powder (AVP-825) in the treatment of acute migraine (The Target Study)", Headache, 2015;55), doi:10.1111/head.12472, pp. 88-100.

Orgel, H. A., Meltzer, E. O., Bierman, W., Bronsky, E., Connell, J. T., Lieberman, P. L., Nathan R., Pearlman D.S., Pence, H. L., Slavin, R.G., et al. J Allergy Clin Immunol., Aug. 1991, vol. 88, No. 2, pp. 257-264.

Food and Drug Administration. FYs 2013-2017 Regulatory Science Report: Locally-Acting Orally Inhaled and Nasal Drug Products, OGD FY13-FY17 Regulatory Science Research Report—1; Feb. 2018. https://www.fda.gov/drugs/genericdrugs/fys-2013-2017-regulatory-science-report-locally-acting-orally-inhaled-andnasal-drug-products. Accessed [Nov. 20, 2019], 14 pages.

"Nasal Spray and Inhalation Solution, Suspension, and Spray Drug Products—Chemistry, Manufacturing, and Controls Documentation; Guidance for Industry", CDER, Jul. 2002, 49 pages.

Srisiwat, Chatchawan et al., "A preliminary study of intranasal epinephrine administration as a potential route for anaphylaxis treatment," Asian Pac J Allergy Immunol 2016:34, pp. 38-43.

Costantino, Henry R., et al., "Intranasal delivery: Physiochemical and therapeutic aspects", International Journal of Pharmaceutics, 337 (2007), pp. 1-24.

SIGMA-ALDRICH product page for Sodium dihydrogen phosphate, downloaded Apr. 27, 2021 from https://www.sigmaaldrich.com/catalog/product/mm/106370?lang=en&region=US, 3 pages.

Sicherer, S. H., Simons, F. E. R., Section On, A. and Immunology. Epinephrine for First-aid Management of Anaphylaxis. Pediatrics . 2017b; 139(3), 2 pages.

Gang, Cheng, et al., A Biopharmaceutics 5th Edition, 2019, National Pharmacopoeia Committee, Chinese Medicine (2019).

Honghao, Cai, Xue, Yuntao, Luo, Jun and Wanjie, "Pharmacopoeia of the People's Republic of China", 2015 Edition, China Medical Science and Technology Press.

Jing, Yao, et al., "Application Guide for Pharmaceutical Excipients", China Medical Science and Technology Press (2011).

Singh, Alok Pratap, et al., "SLN approach for nose-to-brain delivery of alprazolam", Drug Delivery and Translational Research, 2012, vol. 2, Issue 6, pp. 498-507.

FDA Guidance for Industry (Chemistry, Manufacturing & Controls Documentation): Metered-Dose Inhaler (MDI) & Dry Powder Inhaler (DPI) Drug Products—Quality Considerations (Oct. 1998), 50 pages.

Kosfeld, Michael, et al., "OxyContin increases trust in humans", Nature, vol. 435, Jun. 2, 2005, pp. 673-676.

Benedict, Christian, et al., "Intranasal Insulin to Improve Memory Function in Humans", Neuroendocrinology, 2007, vol. 86, pp. 136-142.

Freiherr, Jessica, et al., "Intranasal Insulin as a Treatment for Alzheimer's Disease: A Review of Basic Research and Clincial Evidence", CNS Drugs 2013, vol. 27, pp. 505-514.

Reger, M., et al., "Effect of intranasal insulin on cognition in memory impaired older adults: Modulation by APOE genotype", Neurobiology of Aging, 2006, vol. 27, pp. 451-458.

Jin, Kunlin, et al., "Cerebral Neurogensis Is Induced by Intranasal Administration of Growth Factors", Neurol. 2003, vol. 53, pp. 405-409.

Sherr, Jennifer, et al., "Glucagon Nasal Powder: A Promising Alternative to Intramuscular Glucagon in Youth with Type 1 Diabetes", Diabetes Care 2016, vol. 39, pp. 555-562.

Grassin-Delyle, Stanislas, et al., "Intranasal drug delivery: An efficient and non-invasive route for systemic administration: focus on opioids", Pharmacology & Therapeutics, 2012, vol. 134, pp. 366-379.

Operation Manual (Original), Mini Spray Dryer B-290 Buchi Labortechnik AG, May 31, 2016, 82 pages.

Aundhia, C.J., et al., "Spray Drying in the Pharmaceutical Industry—A Review", Indo American Journal of Pharm Research. 2011:2(1), Jun. 15, 2011, pp. 125-138.

Goyal, Sandhya, et al., "Brain Targeting Through Nasal Route: An Overview on Transport Mechanism, Delivery Systems and Evaluation", 2013, World Journal of Pharmacy and Pharmaceutical Sciences, vol. 2, Issue 4, pp. 1607-1640.

EMA Guideline: Guideline on the Pharmaceutical Quality of Inhalation and Nasal Products, Jun. 2006, 27 pages.

Obaidi, Mohammad, et al., "Improved Pharamacokinetics of Sumatriptan With Breath Powered Nasal Delivery of Sumatriptan Powder", Headache, 2013,vol. 53, pp. 1323-1333.

Fuseau, Eliane, et al.,, "Clinical Pharmacokinetics of Intranasal Sumatriptan", Clin Pharmacokinet., 2002, vol. 41(11), pp. 801-811.

Krieter, Phillip, et al., "Pharamacokinetics Properties and Human Use Characteristics of an FDA-Approved Intranasal Naloxone Product for the Treatment of Opioid Overdose", The Journal of Clinical Pharamacology, May 5, 2016.

Naloxone intranasal (Rx) Information Sheet, Medscape, available online Nov. 22, 2015.

Boström, Emma, et al., "In Vivo Blood-Brain Barrier Transport of Oxycodone in the Rat: Indications for Active Influx and Implications for Pharmacokinetics/Pharmacodynamics", Metabolism and Disposition, vol. 34, No. 9, (2006), 8 pages.

* cited by examiner

TREATMENT WITH POWDERED INTRANASAL EPINEPHRINE

CROSS-REFERENCE TO RELATED APPLICATIONS

This application is a U.S. National Stage application under 35 U.S.C. § 371 of International Application PCT/IL2021/050288, filed Mar. 16, 2021, which is a continuation of U.S. application Ser. No. 17/135,528, filed Dec. 28, 2020, now U.S. Pat. No. 11,400,045, which claims the benefit of priority to U.S. provisional application 62/989,913. PCT/IL2021/050288 also claims benefit to U.S. provisional application 62/989,913. Benefit of the filing date of each of these prior applications is hereby claimed. Each of these prior applications is hereby incorporated by reference in its entirety.

TECHNICAL FIELD

Disclosed are dry powder compositions for intranasal administration of adrenergic receptor agonists, methods for their preparation and uses thereof in medical treatment.

PRIOR ART

Several publications referred to herein are indicated by Arab numerals in parentheses. These publications may be considered relevant as background for the presently disclosed subject matter. A full list of these publications appears at the end of the description, immediately preceding the claims.

BACKGROUND

Intranasal Drug Delivery

Intranasal delivery has a number of compelling advantages over other routes of administration, namely its non-invasiveness, rapid attainment of therapeutically relevant concentrations to the bloodstream, no first-pass metabolism, and ease of administration. Viable nasal delivery technologies are expected to enable the development of innovative pharmaceutical formulations and medicaments of novel as well as approved active pharmaceuticals ingredients by delivery via novel routes of administration.

The intranasal delivery of drugs utilizes devices of several types, such as nebulizers, pressurized devices, dry powder sprayers, and bi-directional nasal devices.

Anaphylaxis is a systemic and life-threatening allergic reaction characterized by anaphylactic shock associated with a critical decrease in blood pressure and deterioration in consciousness. The most frequent triggers of severe anaphylactic reactions are drugs, insect venoms, and foods [(1), (2)]. Epinephrine is currently a universally recommended as the initial drug of choice for the treatment of anaphylaxis [3), (4), (5)] providing a unique effect on body systems potentially involved in anaphylaxis.

Epinephrine

Epinephrine acts on both α- and β-adrenergic receptors. Through its action on α-adrenergic receptors, epinephrine decrease the vasodilation and increased vascular permeability that occurs during anaphylaxis, which can lead to loss of intravascular fluid volume and hypotension. Through its action on β-adrenergic receptors, epinephrine causes bronchial smooth muscle relaxation and helps alleviate bronchospasm, wheezing and dyspnea that may occur during anaphylaxis. Epinephrine is also known to alleviate pruritus, urticaria, and angioedema and may relieve gastrointestinal and genitourinary symptoms associated with anaphylaxis because of its relaxant effects on the smooth muscle of the stomach, intestine, uterus, and urinary bladder. Through the activation of α- and β-adrenergic receptors, epinephrine functionally antagonizes all of the important pathomechanisms of anaphylaxis by vasoconstriction, reduction of vascular permeability, bronchodilatation, edema reduction, and positive inotropy in the heart (6).

Epinephrine is currently available for use in only an injectable dosage form, in ampules or in auto-injectors (7). Each auto-injector contains a single dose of epinephrine and the recommended dose is 0.3 mg/0.3 mL or 0.5 mg/ml epinephrine injection for single-use. Repeat injections may be needed with severe persistent anaphylaxis.

Failure to administer epinephrine promptly has been identified as the most important factor contributing to death in patients with systemic anaphylaxis. Hence, it is recommended that patients with history of severe anaphylactic reactions or the caregivers have epinephrine injection readily available for first aid treatment (8). The use of epinephrine injection is however limited due to its potential drawbacks. Research has been conducted to find alternatives to epinephrine auto-injectors. The feasibility of epinephrine administration via intranasal (IN) route in humans has been demonstrated in clinical studies. In emergency situations, intranasal delivery could be considered as an alternative route of epinephrine injection due to the convenience in drug administration.

When given subcutaneously or intramuscularly, epinephrine has a rapid onset and short duration of action.

The results of a recent study (INS015-17-112) comparing two formulations of epinephrine nasal spray, aqueous (AQ) and hydro-alcoholic (HA) (both investigational products were developed by Insys) to EpiPen® in adults with seasonal allergy reported that epinephrine was rapidly absorbed following single 6 mg AQ and HA doses vs. EpiPen® 0.3 mg IM, with epinephrine plasma concentrations above 100 pg/mL within 5 minutes and median $T_{max}$ within 5-16 minutes for AQ, 3-10 minutes for HA, and 5 minutes for EpiPen®. Allergen challenge mainly impacted epinephrine absorption, with $C_{max}$ increased 1.72-fold for AQ and 1.43-fold for HA, with minor change in AUC for AQ or HA; EpiPen® exposure was unaffected (9).

Similarly, another study in healthy volunteers showed that intranasal epinephrine at 5 mg in saline formulation had significant systemic absorption which was comparable to IM epinephrine 0.3 mg with the average area under the curve (AUC) values at 0-120 minutes of 18.3 and 19.4 ng*min/mL, respectively (9).

The pharmacokinetic (PK) characteristics of epinephrine from the literature are presented in Table 1 (9):

TABLE 1

| Pharmacokinetic Characteristics of Epinephrine via Intramuscular and Intranasal routes | | | | |
|---|---|---|---|---|
| Epinephrine formulation | $T_{max}$ (min) | $C_{max}$ (pg/mL) Mean (±SD) | $C_{baseline}$ (pg/mL) Mean (±SD) | $AUC_{0-120}$ min (ng · min/mL) |
| Epinephrine 0.3 mg IM | 67 ± 43 | 309 ± 88 | 35 ± 23 | 18.3 ± 9.3 |
| Epinephrine 5 mg IN | 70 ± 17 | 386 ± 152 | 8 ± 6 | 19.4 ± 12.1 |

Dry powders are used in intranasal drug delivery due to the many advantages of using this dosage form including the improved stability, administration of larger doses and lack of microbial growth (no need for preservatives). The administration of intranasal powders may improve patient compliance, especially where the smell and taste of the delivered solution composition comprising excipients is unpleasant. Compared to drug solutions, the administration of powders can result in a prolonged contact with the nasal mucosa. Powder form is suitable for delivery of both small molecules and biologicals, especially peptides, hormones and antibodies.

WO2019/038756 describes a pharmaceutical composition in a form of dry powder for intranasal administration, the composition comprising solid particles of at least one active agent and solid particles of a carrier/disaggregation agent/deagglomerating agent/diluent, the pharmaceutical composition being substantially free of excipients other than the solid diluent, the pharmaceutical composition having at least 90% of the particles of the active agent with a mean particle size of 10-30 microns and less than 10% of the particles of the active agent with a mean particle size equal to or below 5 microns, and having the particles of said disaggregation agent/diluent with a mean particle size of 50-200 microns.

SUMMARY OF INVENTION

Disclosed herein is a pharmaceutical composition comprising as active agent an anti-anaphylactic adrenergic receptor agonist in the form of dry powder for intranasal administration, said composition comprising a first type of solid particles comprising at least one active agent in combination with at least one functional additive, and a second type of solid particles comprising a pharmaceutically acceptable carrier/diluent/disaggregating/deagglomerating agent, wherein at least about 90% of said first type particles are of a mean particle size of about 10-30 microns and less than about 10% of said first type particles are of a mean particle size equal to or below about 10 microns and said second type particles are of a mean particle size greater than that of the first type particles. The second type particles are of a mean particle size of about 50-200 microns.

In all aspects and embodiments of the present disclosure, the pharmaceutical composition of can be substantially free of excipients other than said at least one functional additive comprised in said first type particles and said carrier comprised in said second type particles.

In embodiments of the disclosed pharmaceutical composition the active agent can be any one of epinephrine, norepinephrine, dopamine or antihistamine or pharmaceutically acceptable salts or derivatives thereof, but is not limited thereto. In some specific embodiments, the active agent is epinephrine or a pharmaceutically acceptable salt thereof, which can be any one of pharmaceutically acceptable bitartrate, hydrochloride or borate salt thereof, as well as hydrates and anhydrates thereof.

The functional additive comprised in said first type particles can be any one of a buffering agent, glidant or lubricant. The buffering agent comprised in said first type particles can be sodium di-hydrogen phosphate, but is not limited thereto.

In embodiments of the presently disclosed pharmaceutical composition the ratio between the at least one pharmaceutically active agent and the at least one functional additive in the first type particles is predetermined, according to chemical and other properties of the specific constituents.

In embodiments of the presently disclosed pharmaceutical composition the carrier/diluent/disaggregating/deagglomerating agent can be any one of lactose monohydrate, lactose, a lactose functional analogue, or any mixture of at least two thereof. Alternatively, the carrier/diluent/disaggregating/deagglomerating agent can be any one of dextrose, sorbitol, mannitol, maltitol and xylitol, a cellulose or cellulose derivative, or starch or starch derivative.

In embodiments of the presently disclosed pharmaceutical composition the weight ratio between said first type particles and said second type particle can be between 1:9 to 9:1, for example 1:9, 2:8, 3:7, 4:6, 5:5, 6:6, 7:3, 8:2 or 9:1, and any mid-ratios therebetween.

In a specific embodiment, the present disclosure provides an epinephrine pharmaceutical composition in the form of dry powder for intranasal administration, comprising as active agent epinephrine or a pharmaceutically acceptable salt thereof, said composition comprising a first type of solid particles comprising epinephrine or a pharmaceutically acceptable salt thereof in combination with a physiologically acceptable buffering agent, and a second type of solid particles comprising lactose monohydrate as carrier, wherein at least about 90% of said first type particles are of a mean particle size of about 10-30 microns and less than about 10% of said first type particles are of a mean particle size equal to or below about 10 microns and said second type particles are of a mean particle size greater than that of the first type particles, providing a metered therapeutically effective nominal dose of said epinephrine or pharmaceutically acceptable salt thereof. In this epinephrine pharmaceutical composition the molar ratio between the epinephrine bitartrate to sodium dihydrogen phosphate can be 0.9:1. The therapeutically effective amount of epinephrine in this epinephrine pharmaceutical composition is essentially equivalent to about 0.3 mg or 0.5 mg epinephrine administered i.m. (intra-muscularly, also referred to as IM).

Further disclosed herein is a disposable dose unit form for intranasal administration to a subject of a pharmaceutical composition according to any one of claims 1 to 12, wherein said dose unit is loaded with a predetermined single dose of the composition and provides the subject with a metered dose the pharmaceutically active adrenergic receptor agonist. The disposable dose unit form can be loaded with a predetermined single dose of the composition and provides the subject with a metered dose epinephrine.

In some embodiments, the dose unit is loaded with a predetermined single dose of the composition and provides the subject with a metered dose epinephrine being equivalent to about 0.3 mg or 0.5 mg epinephrine administered intramuscularly.

a. In a further aspect disclosed herein is a kit for intranasal administration of epinephrine comprising at least one dose unit for intranasal administration comprising a pharmaceutical composition as disclosed herein and instructions for use.

Still further, provided herein is a method of treating anaphylactic shock in a patient in need thereof, said method comprising administering to said patient a therapeutically effective amount of a composition as disclosed herein or at least one dose unit as disclosed herein.

In a specific embodiment, the present disclosure provides a method of treating anaphylactic shock in a patient in need thereof, said method comprising administering to said patient a therapeutically effective amount of an epinephrine composition as defined herein or at least one epinephrine dose unit as disclosed herein.

BRIEF DESCRIPTION OF THE DRAWINGS

In order to better understand the subject matter that is disclosed herein and to exemplify how it can be carried out in practice, embodiments will now be described, by way of non-limiting example only, with reference to the accompanying drawings, in which.

DESCRIPTION OF EMBODIMENTS

Figure 1:
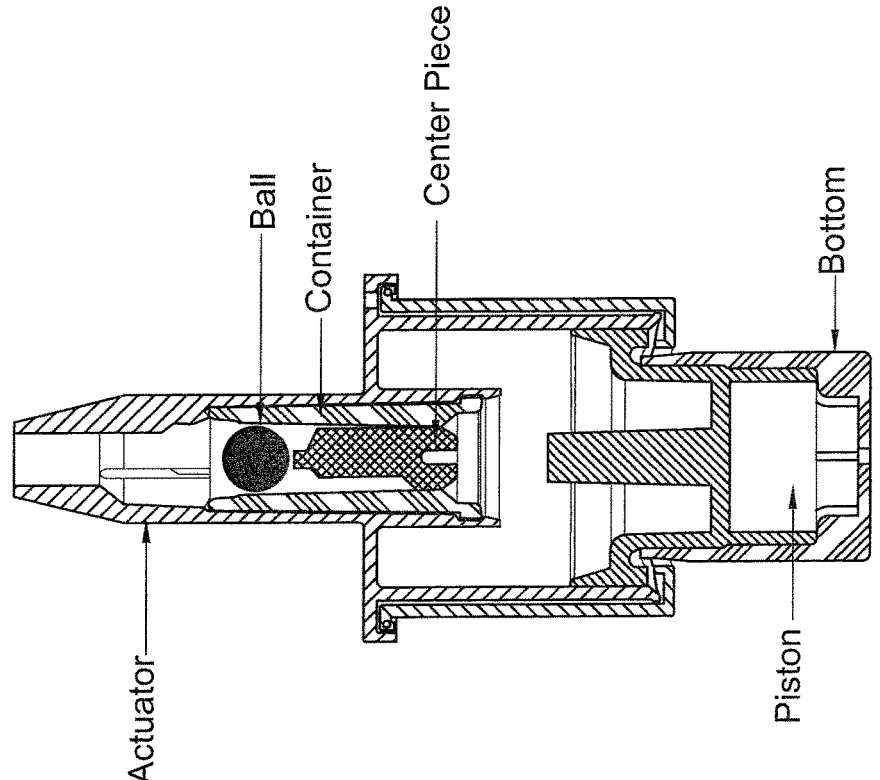
FIG. 1 exemplary Unit Dose Powder Device and its components for nasal administration FIG. 2 schematic representation of the modified spray-dryer apparatus used in the present examples, as described in Example 1
Figure 1:
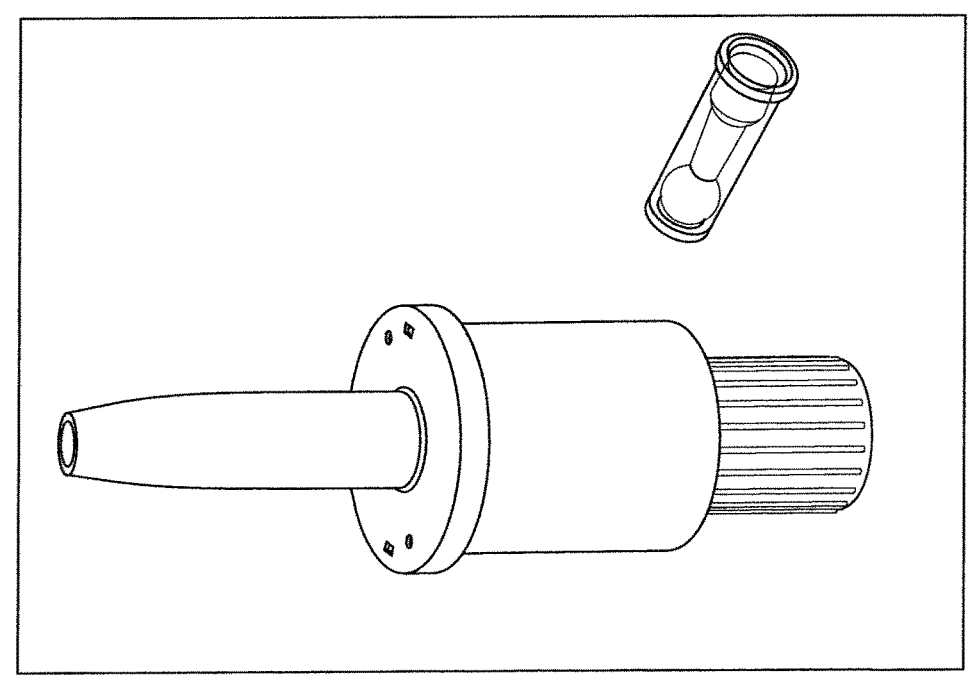

Disclosed herein are novel formulations the form of dry powder, for intranasal administration of pharmaceutically active agent/s. Generally, a formulation according to the present disclosure comprises two types of solid particles, a first type of essentially spherical particles comprising the pharmaceutically active agent in combination with a functional additive, and a second type of irregularly shaped particles comprising an essentially inert carrier/diluent/disaggregating/deagglomerating agent.

In a first aspect, the present disclosure relates to a pharmaceutical composition in the form of dry powder for intranasal administration, comprising a first type of solid particles comprising at least one pharmaceutically active agent in combination at least one functional additive, and a second type of solid particles comprising a pharmaceutically acceptable carrier/diluent/disaggregating/deagglomerating agent, in which at least about 90% of said first type particles are of a mean particle size of about 10-30 microns and less than about 10% of said first type particles are of a mean particle size equal to or below about 10 microns and said second type particles are of a mean particle size greater than that of the first type particles, such as a mean particle size of about 50-200 microns.

Active agents for intranasal administration in dry powder form are usually produced by milling techniques. As a result, their particle size distribution is broad and the particles are usually non-spherical and non-uniform. The presence of active agent particles of less than 5 microns ($\mu$m) should however be avoided. Such very small particles may reach the lung mucosa by nasal spraying or by inhaling, which completely unacceptable for intranasal administration from the safety point of view. Therefore, the size distribution of the presently disclosed compositions, wherein the major part (about 90%) of the particles comprising the pharmaceutically active agent have a mean size of 10-30 microns, and only less than 10% of the particles are of a mean diameter of less than 5 microns their use in nasal spraying renders them beneficial for the intranasal administration.

In all embodiments of all aspects of the present disclosure, the pharmaceutically active agent can be an adrenergic receptor agonist, for example, but not limited to any one of epinephrine, norepinephrine, dopamine or antihistamine or pharmaceutically acceptable salts or derivatives thereof. A specific pharmaceutically active agent is, but not limited to, epinephrine or a pharmaceutically acceptable salt thereof, such as, but not limited to any one of bitartrate, hydrochloride or borate salts of epinephrine.

In all embodiments of all aspects of the present disclosure, the said functional additive can be any one of a buffering agent, glidant or lubricant and others. A buffering agent can be but is not limited to sodium di-hydrogen phosphate, potassium di-hydrogen phosphate, Tris-buffer, or any other physiologically and pharmaceutically acceptable buffer which can elevate pH. The functional additive is compatible with the active agent.

In all embodiments of all aspects of the present disclosure, the inert carrier/diluent/disaggregating/deagglomerating agent can be any one of lactose monohydrate, lactose, a lactose functional analogue, or any mixture of at least two thereof. A lactose functional analogue can be but is not limited to dextrose, sorbitol, mannitol, maltitol and xylitol, or a cellulose or cellulose derivative or starch or starch derivative. For example, lactose powder is used as a carrier in nasal drugs and has no effect on drug absorption or the nasal epithelium in short and long term follow up [(10), (11), (12)].

In all aspects and embodiments of the present disclosure the present pharmaceutical composition is substantially free of excipients other than the at least one functional additive comprised in said first type particles and the inert carrier/diluent/disaggregating/deagglomerating agent comprised in said second type particles.

The pharmaceutical composition according to the present disclosure can be contained in disposable dose units for intranasal administration, providing predetermined metered dose of epinephrine. An example of such dose unit is illustrated in FIG. 1, which shows Unitdose Powder Device (UDS), manufactured by Aptar Pharma. Devices of this type for powder spraying are user friendly and designed to enable systemic delivery of small and accurately metered doses of drug formulations by patients or caregivers who are not healthcare professionals or medically trained.

Thus, in a further aspect the present disclosure relates to a dose unit form, specifically a disposable dose unit form, for intranasal administration to a subject of a pharmaceutical composition according to all aspects and embodiments of the present disclosure, wherein the dose unit is loaded with a predetermined dose of the composition and provides the subject with a metered dose the pharmaceutically active ingredient comprised in the composition. As shown in the following Examples, the dose unit device loaded with epinephrine-buffer combination exhibits good product stability under normal and accelerated storage conditions.

Bi-dose and multi-dose intranasal administration devices can be used. Such powder delivery devices generally have a disposable drug containing member and a reusable device body that can be packaged along with a number of drug-containing members. The disposable drug containing member contains the powdered drug within standard size inhalation capsules. Each capsule content equals to one dose.

In addition, syringe-driven and pump-driven spraying atomizers used for delivery of a variety of nasal medications can be used for the delivery of the present pharmaceutical composition.

In specific embodiments of all aspects of the present disclosure, the pharmaceutically active ingredient is epinephrine.

Figure 3:
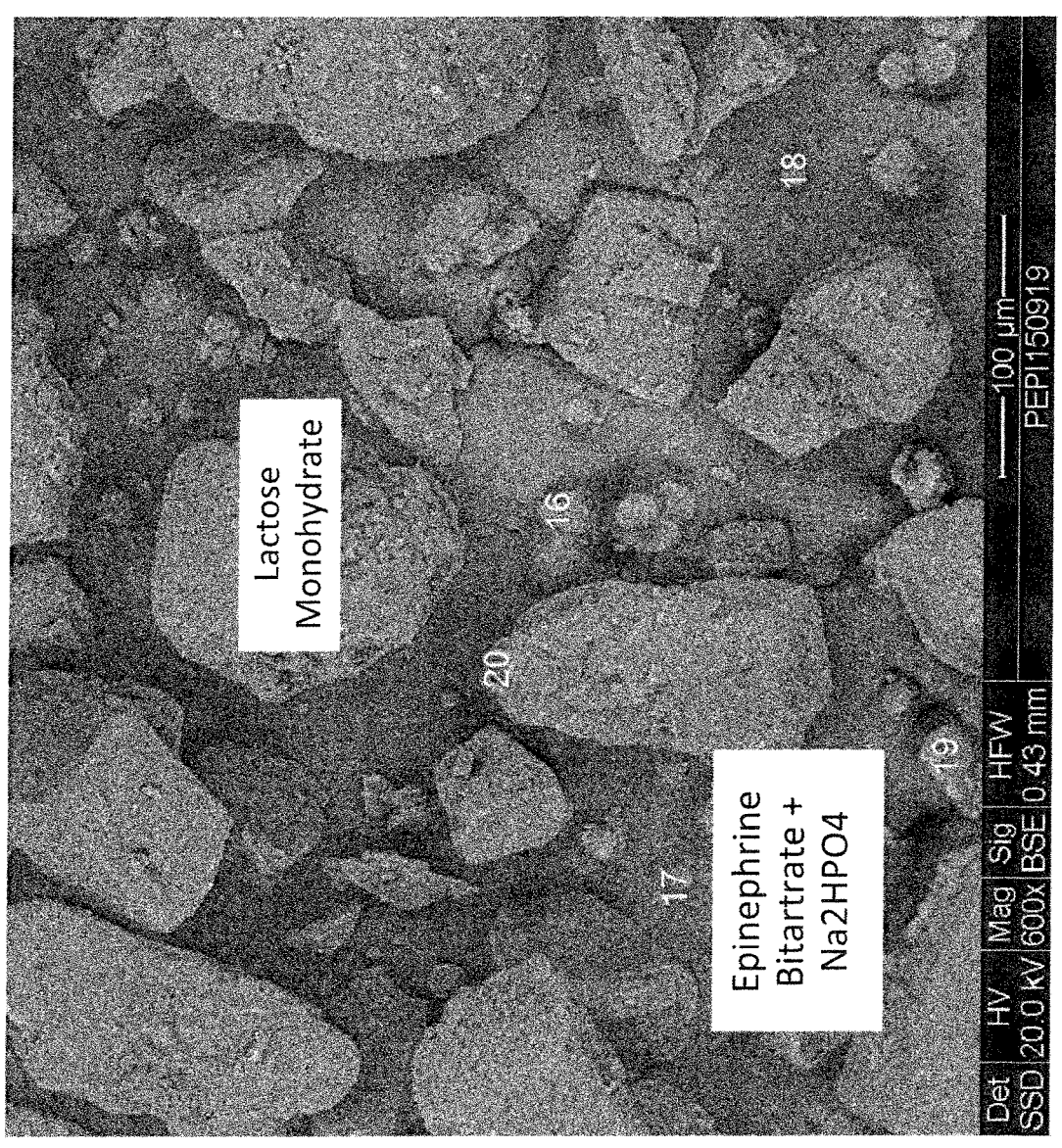
FIG. 3 SEM images of lactose monohydrate (large irregular particles) and epinephrine bitartrate/sodium di-hydrogen phosphate particles (small spherical particles) of the dry powder intranasal formulation obtained in Example 2.

One specific formulation of epinephrine microspheres powder for intranasal administration disclosed herein is also referred to as FMXIN002. Generally, this formulation comprises solid essentially spherical particles of epinephrine bitartrate as the pharmaceutically active ingredient and sodium di-hydrogen phosphate as the pH-adjusting functional additive (first type of particles) and solid irregularly shaped particles of lactose monohydrate as a carrier/diluent/disaggregating/deagglomerating agent (second type of particles). Surprisingly, as shown in FIG. 3 and Example 2, the first type smaller particles contained not only the epinephrine, but also the sodium di-hydrogen phosphate, which was unexpected and is of major advantage reducing any effects of local irritation by epinephrine, as herein discussed. FMXIN002 can be administered intranasally by intranasal delivery devices, for example a disposable intranasal device as described above. In more detail, FMXIN002 epinephrine microspheres powder is composed of two populations of particles: most of the epinephrine bitartrate and buffer (pH adjusting agent) particles (drug particles), namely at least about 80%, 85%, 90% of the particles or more, have an optimal mean diameter of 10-30 μm, and less than about 10%, 9%, 8%, 7%, 6% or 5% of drug particles have a mean diameter of less than about 5 μm, preventing lung inhalation. The lactose monohydrate particles are larger, and ranges between about 50 to about 200 μm. An in vitro study has demonstrated that immediately after deposition of the powder in the nasal cavity, epinephrine dissolves in the nasal fluid and is rapidly absorbed through the nasal epithelia due to the spherical and small particle size, and high-water solubility (10). In specific embodiments, the molar ratio between the epinephrine bitartrate to sodium dihydrogen phosphate is 0.9:1 (weight ratio of 1.67/1).

As mentioned, the first type particles comprise both the active drug and the functional additive, for example epinephrine or salt thereof and a buffering agent such as sodium di-hydrogen phosphate. In other embodiments, buffer materials can be added to epinephrine microsphere to provide pharmaceutical acceptable pH. Some epinephrine salts such as epinephrine bitartrate have acidic pH below 3.5. As mentioned, the administration of microspheres comprising only these salts can cause irritation and discomfort to nasal mucosa. In such cases adjusting the pH in the nasal cavity is recommended, for example by the addition of pH elevating buffers, as described and exemplified herein.

The pH-adjusting agent (buffering agent), for example small amounts of physiological phosphate buffer (sodium di-hydrogen phosphate), provides for maintaining an adequate pH of the epinephrine solution after its dissolution in the nasal mucus, and prevent local irritation or any other discomfort to the patient.

The disclosed pharmaceutical composition can be prepared by a modified spray drying method, as described for example in WO2019/038756. An apparatus for the preparation of the disclosed pharmaceutical composition in the dry powder form essentially comprises the following components:

a) A spray-drying chamber capable of spray-drying a clear and homogeneous solution of the active agent and the functional additive to obtain dry powder particles of said first type, specifically wherein said solution is free of other excipients;

b) A cyclone separator capable of receiving the dry powder particles and the moist air stream from the spray-drying chamber, separating said particles from the moist air through vortex separation, exhausting the air and transferring the separated particles to a receiving chamber through a bag filter; and c) A receiving chamber pre-filled with a carrier/diluent/disaggregating/deagglomerating agent and adapted for receiving the separated dry powder particles from the cyclone separator, stirring and homogenising said particles with the carrier/diluent/disaggregating/deagglomerating agent to obtain the presently disclosed pharmaceutical composition in dry powder form. The carrier/diluent/disaggregating/deagglomerating agent is capable of colliding and continuously in-situ blending with the particles during the stirring in the receiving chamber, thereby preventing their aggregation and preserving their original size and shape.

The spray-drying chamber is equipped with nozzles, used to produce droplets of the active agent solution, to control the droplet and powder particle size and to maximise heat transfer and the rate of solvent vaporisation. The droplet size may range from 20 to 180 μm, depending on a particular nozzle used. In the present embodiments, the sprayed solution of the active agent is free of any carrier/diluent/disaggregating/deagglomerating agent. The nozzles are designed to spray the solution of the active agent into a hot air flow, thereby achieving a thorough mixing and uniform distribution of the hot air flow and sprayed solution in the spray-drying chamber to allow for substantially complete evaporation of liquids and drying of solid particles of the active agent from the mixture throughout said chamber.

At the laboratory scale, the stirring and homogenisation is achieved by using a magnetic stirrer and a magnetic bar of appropriate size, in addition to the rotation of the receiving chamber. At industrial scale, the stirring and homogenisation may be achieved by using a mechanical stirrer of appropriate size and form, or moving, rotation and vibration of the whole receiving chamber. A conventional spray-drying apparatus contains the empty receiving chamber collecting the dry powder particles of an active agent. This receiver is emptied from time to time in order to ensure the continuous process. In contrast, the present application discloses the receiving chamber pre-filled with a continuously stirred carrier/diluent/disaggregating/deagglomerating agent for preventing aggregation of the dry powder particles and preserving their original size and shape.

Generally, the preparation of presently disclosed pharmaceutical composition by use of the described apparatus comprises the following steps:

A. Preparing a clear and homogeneous solution of at least epinephrine bitartrate or other pharmaceutically acceptable salt thereof or another active epinephrine analogue and a pH-adjusting agent (buffering agent, for example sodium di-hydrogen phosphate) in an organic solvent (for example acetone) or solvent mixture, in a solvent-water or water-miscible solvent mixture, or in water.

B. Filling the receiving chamber with a canier/diluent/disaggregating/deagglomerating agnet and continuously stifling the canier/diluent/disaggregating/deagglomerating agent in the receiving chamber;

C. Streaming the solution prepared in step (A) together with hot air or gas to the spray-draying chamber, spray-drying the solution in the spray-drying chamber to obtain dry powder particles of said at least one active agent in a moist air or gas, and transferring the obtained dry powder particles and the moist air or gas stream to the cyclone separator;

D. Separating the particles from the moist air or gas through vortex separation in the cyclone separator, exhausting the air or gas and transferring the separated particles to the receiving chamber through a bag filter;

E. Stirring and homogenising said particles obtained in step (D) with the carrier/diluent/disaggregating/deagglomerating agent in the receiving chamber to obtain the presently disclosed pharmaceutical composition in dry powder form; wherein said carrier/diluent/disaggregating/deagglomerating agent is capable of colliding and continuously in-situ blending with the particles during the stirring in the receiving chamber, thereby preventing their aggregation and preserving their original size and shape; and F. Optionally, additional mixing of the pharmaceutical composition obtained in (E) with an additional amount of the canier/diluent/disaggregating/deagglomerating agent to achieve the desired active agent-to-carrier ratio in said pharmaceutical composition.

In a further aspect, the present disclosure provides method for treating and/or alleviating a medical condition responsive to an adrenergic receptor agonist, as defined herein, for example by not limited to epinephrine and pharmaceutically acceptable salt thereof. The method of treatment according to the present invention comprises intranasal administration to a subject in need a therapeutically effective amount of an adrenergic receptor agonist pharmaceutical composition as disclosed herein, optionally where loaded in a dose form unit as disclosed herein. In specific embodiments, the adrenergic receptor agonist is epinephrine, more specifically epinephrine bitartrate, at a therapeutically effective amount of IN dose of from about 1.6 mg to about 3.2 mg. Treatment begins with administration of a single dose. If the patient is not stabilized within few minutes, additional doses can be repeatedly administered within 5-15 minutes, and patient is transferred to hospital for further observation. Patients prone to anaphylactic shock or caregiver should be routinely equipped with 2 device packages. Intranasal administration can be to one or both nostrils, as instructed.

Further provided herein is a kit for the treatment of anaphylaxis. The kit comprises at least one dose unit, preferably two dose units of epinephrine as disclosed herein and instructions for use.

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The terminology used herein is for describing particular embodiments only and is not intended to be limiting of the invention. The term "comprising" and "comprises", used in the claims, should not be interpreted as being restricted to the components and steps listed thereafter; they do not exclude other components or steps. They need to be interpreted as specifying the presence of the stated features, integers, steps and/or components as referred to, but does not preclude the presence and/or addition of one or more other features, integers, steps or components, or groups thereof. Thus, the scope of the expression "a composition comprising A and B" should not be limited to compositions consisting only of components A and B. Also, the scope of the expression "a method comprising the steps X and Z" should not be limited to methods consisting exclusively of those steps.

Definitions

The terms "drug", "active substance", "API" (Active Pharmaceutical Ingredient) or "active principle" or "active ingredient", "pharmaceutically active agent", "pharmaceutically active ingredient", "active substance", "active molecule", "active compound" and the like used herein interchangeably, refer to a pharmaceutically active substance that provides a therapeutic/physiological effect to a patient, and can also refer to a mixture of at least two thereof.

The terms "formulation", "pharmaceutical formulation", "composition" and "pharmaceutical composition" may be used herein interchangeably, and are to be taken to mean a formulation comprising an adrenergic receptor agonist, such as but not limited to epinephrine or a pharmaceutically active salt thereof for use in therapy/medicine.

The terms "inert" or "inactive" or "inactive ingredient" or "inert ingredient", as used interchangeably herein refer to components of the pharmaceutical composition, or used in the preparation thereof, that do not instantly react with the active ingredient or adversely affect its properties, or cause any biological effect upon administration to a subject when administered at reasonable amounts to a subject. The general examples of these components are described in "The Handbook of Pharmaceutical Excipients", $4^{th}$ Edition, by Rowe, Sheskey and Weller, Pharmaceutical press, 2003. Additional exemplary list is Inactive Ingredients Guide of the Food and Drug Administration, USA.

"Carrier", "diluent", "disaggregating agent" and "deagglomerating agent" are used herein interchangeably, and refer to an inert ingredient added to the pharmaceutical composition.

A "patient" or "subject" that may be administered with the pharmaceutical composition and/or dose units loaded therewith according to the presently disclosed subject matter. In general, where the drug is an adrenergic receptor agonist as herein described, the "patient" or "subject" is a human, suffering from a medical condition responsive to such agonist. Such conditions may be cardiac arrest and other heart problems, patients prone to anaphylactic shock including all Type 1 allergy patients, asthmatic patients and others.

"An adrenergic receptor agonist" as used herein is to be taken to mean an agent that stimulates a response from adrenergic receptors. An examples of such agonists are epinephrine (adrenaline) and its pharmaceutically acceptable salts. "Epinephrine" as used herein also refers to pharmaceutically active salts thereof.

"pH adjusting agent", "buffering agent" and "buffer" as used herein interchangeably are to be taken to mean any chemical agent that affects the pH of its immediate environment.

The term a composition or substance "substantially free of excipients" is to be taken to mean that it does contain more than 5% of such excipient/s.

The terms "treat", or forms thereof, and the term "alleviate" and the like are to be taken to mean at least partially ameliorate or cure or totally eliminate the patient's condition as defined herein.

The term "intranasal administration" as used herein is to be taken to mean nasal application in one or both nostrils of the subject.

The term "suitable" as used herein is to be taken to mean having the properties that enable providing the defined result.

"About" as used herein generally refers to approximate values. When referred to a dose of drug, or size of particles and the like, "about" should be understood as including the range of a value ±15%. When referred to other values, the term should be understood as including the range of a value ±15%, for example ±15%, ±12%, ±10%, ±8%, ±5%, ±2% or ±1%. Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value.

As used herein, the term "and/or" includes any combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealised or overly formal sense unless expressly so defined herein. Well-known functions or constructions may not be described in detail for brevity and/or clarity.

As used in the specification and claims, the forms "a", "an" and "the" include singular as well as plural references unless the context clearly dictates.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The presently disclosed subject matter is further illustrated by the following examples, which are illustrative only and are not to be construed as limiting the scope of the invention. Variations and equivalents of these examples will be apparent to those skilled in the art in light of the present disclosure, the drawings and the claims herein.

It is appreciated that certain features of the presently disclosed subject matter which are, for clarity, described in the context of separate embodiments, can also be provided in combination in a single embodiment. Conversely, various features of the presently disclosed subject matter, which are, for brevity, described in the context of a single embodiment, can also be provided separately or in any suitable subcombination.

Although the presently disclosed subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as relevant prior art to the presently disclosed subject matter.

DESCRIPTION OF NON-LIMITING EXAMPLES

Materials

Epinephrine bitartrate (TransoPharma); Sodium Phosphate Dibasic Dihydrate (Merck), lactose monohydrate (Meggle Pharma); acetone (BioLab).

Methods

The spray-drying process was carried out using the Mini Spray Dryer B-290 of Büchi Labortechnik AG. A magnetic stirrer (Fried Electric) was placed under the receiver (receiving chamber), a magnetic bar of appropriate size was inserted into the receiver, and then the carrier/diluent/disaggregating/deagglomerating agent was added. The liquid feed containing at least one active agent was prepared by dissolving at least one active compound in the selected solvent or mixture of solvents. Quantification was performed using HPLC and a Dionex HPLC instrument. A FEI Quanta-200 Scanning Electron Microscope (SEM) equipped with an Everhart-Thornley Detector was used to obtain the images of the spray-dried powder. The accelerating voltage of 20 kV was applied to provide magnification from 250 to 10,000 times. In addition, an X-ray Element Analysis Detector (Link ISIS, Oxford Instruments, England) was used to determine particles morphology and chemical composition and their distribution throughout Dry Powder Inhaler (DPI). Particle size was measured using the Malvern Mastersizer 3000 series based on the Light Diffraction method. Epinephrine assay in the compositions was determined using Dionex HPLC-PDA instrument equipped with Chromeleon software; Column & packing: Thermo ODS, 3 $\mu$100×4.6 mm Cat No: 30103-104630 or equivalent Mobile phase A: Buffer:Acetonitrile (95:5, v/v)

Mobile phase B: Buffer:Acetonitrile (55:45, v/v)

Flow rate: 1.2 mL/min

Gradient Table for Sample:

| Time, min | % A | % B |
|---|---|---|
| 0.0 | 95 | 5 |
| 20 | 50 | 50 |
| 21 | 50 | 50 |
| 23 | 95 | 5 |
| 30 | 95 | 5 |

Gradient Table for Standard:

| Time, min | % A | % B |
|---|---|---|
| 0.0 | 95 | 5 |
| 10 | 72.5 | 27.5 |
| 10.5 | 95 | 5 |
| 15 | 95 | 5 |

Injection volume: 20 $\mu$L

Detector PDA: UV, 210 nm; 200-400 nm for identification.

Column temperature: 50° C.

Auto sampler temperature: ambient

Run time 30 min

Diluent: Mobile Phase A

RT of epinephrine peak: 5-7 min

Example 1: Modification of the Commercial Büchi Labortechnik AG Spray-Dryer

Figure 2:
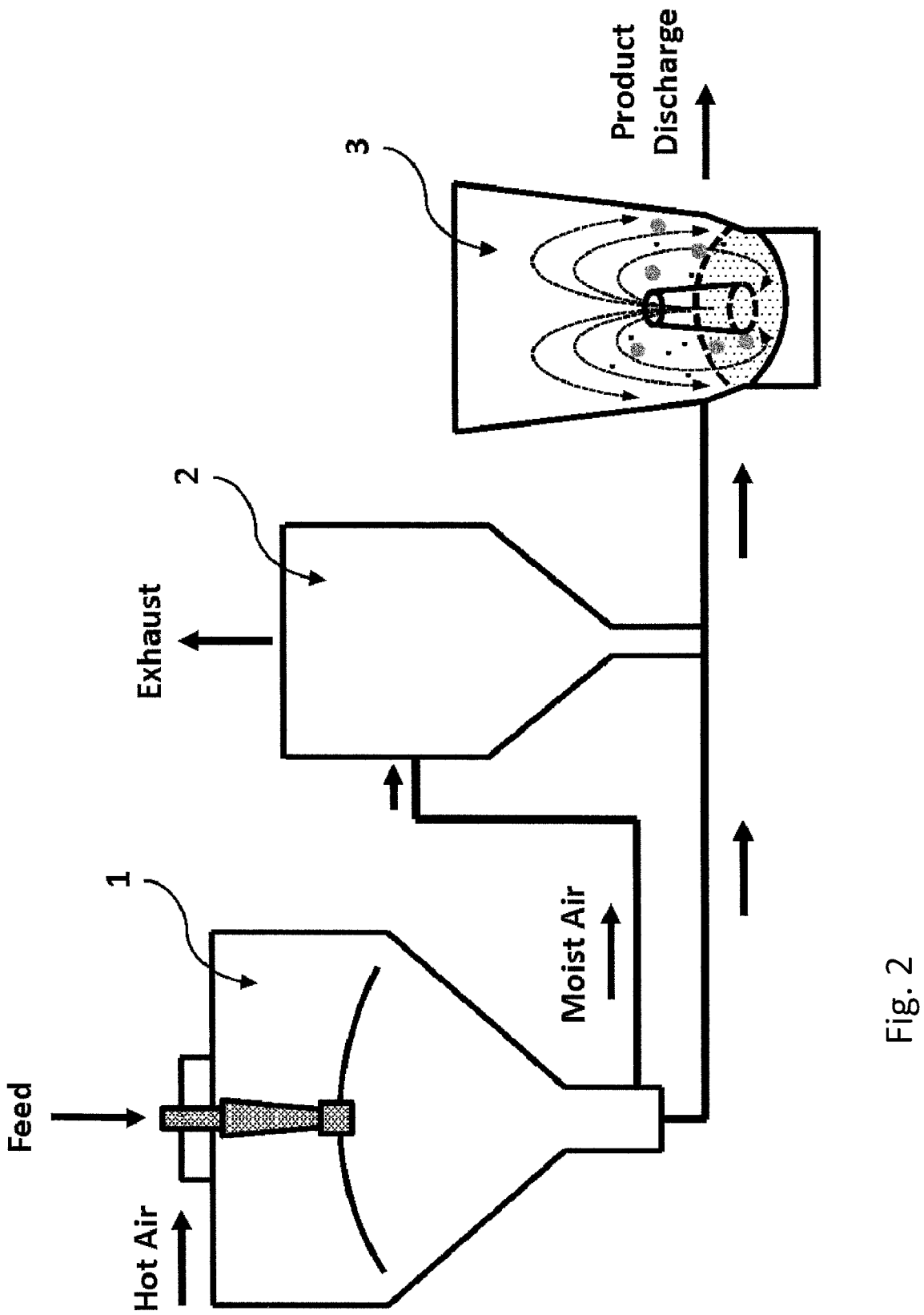

FIG. 2 schematically shows a modified spray dryer used in the present examples. A Mini Spray-Dryer B-290 of Büchi Labortechnik AG was modified by:

1. Addition of a magnetic bar into the glass receiver and placing a magnetic stirrer under the continuously rotating glass receiver of the spray-dryer.
2. Selection of a suitable two-fluids spraying nozzle for spraying the solution containing only the active agent epinephrine (without canier/diluent/disaggregating/deagglomerating agent) into fine droplets suitable for the preparation of 10-30 μm dry powder particles of the active agent. One of the fluids is the clear and homogeneous solution of the active agent, and the second fluid is the drying gas.

The modified spray dryer is suitable for the particles engineering and prevention of agglomeration according to the present disclosure.

Example 2: Epinephrine Bitartrate/Sodium Di-Hydrogen Phosphate Composition with Lactose Monohydrate Epinephrine bitartrate (2.5 g) and sodium di-hydrogen phosphate (1.5 g) were dissolved for 20 min in 15 g of acetone and 20 g water mixture under nitrogen and stiffing at 300 rpm. An appropriate size magnetic bar was placed in the receiver and lactose monohydrate (3.0 g) was added thereto, with the stiffing rate set at 150 rpm. A clear and homogeneous solution of the drug was obtained, and spray-dried using the modified Büchi Mini Spray-Dryer with inlet nitrogen temperature of 130° C. and outlet temperature of 80° C., thereby obtaining a dry powder of epinephrine bitartrate/sodium di-hydrogen phosphate, which was further blended in-situ with lactose monohydrate in the receiver. Stiffing was maintained in the receiver during the entire process. The loading of epinephrine bitartrate/sodium di-hydrogen phosphate in the composition was about 8.7% w/w.

The SEM images presented in FIG. 3 show that the small spherical particles of epinephrine bitartrate/sodium di-hydrogen phosphate have a narrow size distribution of 5-30 μm, and are dispersed between large irregular particles of lactose ranging between 40 □m to 240 μm.

Figure 4:
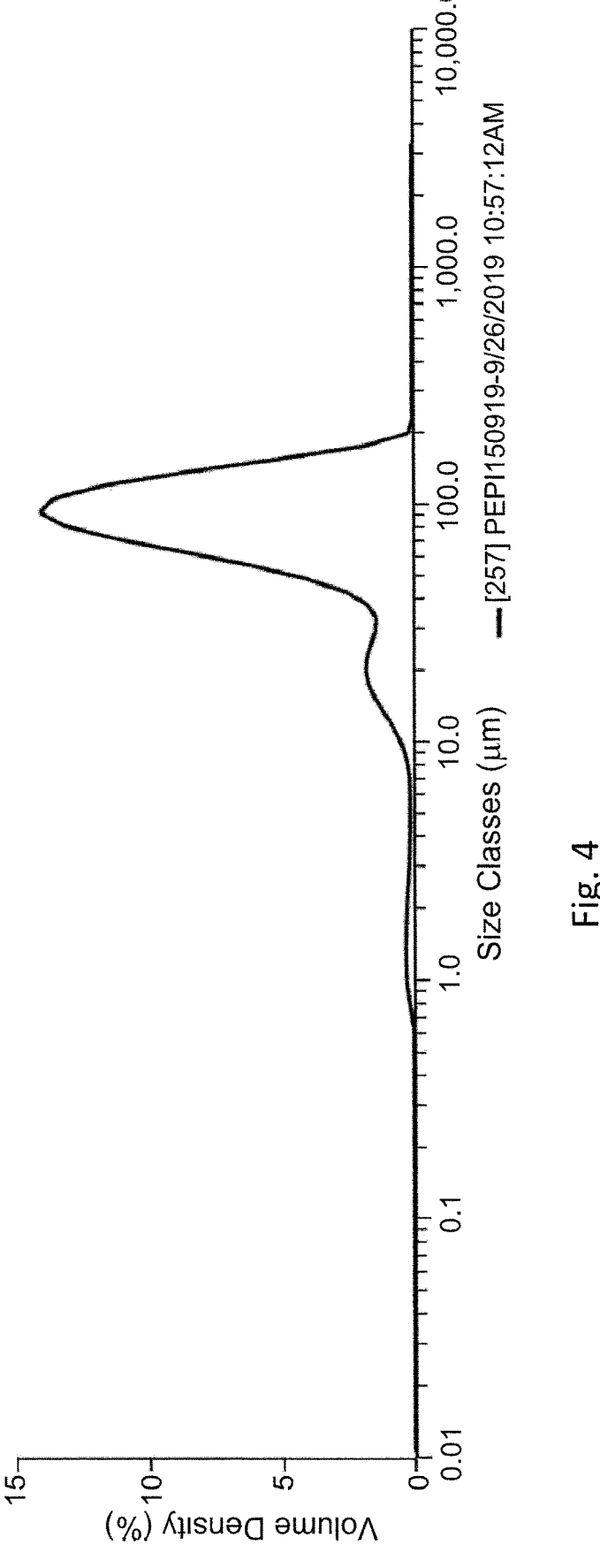
FIG. 4 shows the particle size distribution of the dry powder intranasal formulation obtained in Example 2.

The obtained epinephrine bitartrate/sodium di-hydrogen phosphate composition was subjected to particle size analysis using a Malvern Laser Diffraction instrument. As shown in FIG. 4, the following particle size distribution was obtained: D=21.4 μm, D (50)=82.0 μm and D (90)=133 μm. The amount of the obtained particles having the size less than 10 μm was about 3.7% v/v. 5 μm was about 2.8% v/v. The particle size distribution of epinephrine microspheres thus meets powder Bulk Drug Product specification and safety requirements (11, 13)

Example 3: Epinephrine Bitartrate Drug-Device Combination Product Preparation Aptar Unit-Dose Powder disposable devices, assembled according to the manufacturer's guidelines, were filled with the epinephrine bitartrate/sodium di-hydrogen phosphate composition prepared in Example 2. Each device contained 35 mg of powder including 1.6 mg of epinephrine bitartrate.

Example 4: Stability Data of Epinephrine Drug-Device Combination Product Under Accelerated Aging Conditions The epinephrine bitartrate combination products prepared in Example 3 were subjected to accelerated aging conditions at 40° C.±2° C. and 75% RH±5% RH. Three months stability data are presented in Table 2.

TABLE 2

| | | | | | | |
|---|---|---|---|---|---|---|
| | | | Stability data | | | |
| Item | Testing interval, months | Appearance | Assay (HPLC) | Impurities/related substances | Water content | pH |
| Specifications | | Disposable plastic device; white color; no visible damage | 1.6 ± 0.32 mg/device (80.0-120.0%) | A. ≤0.3% B. ≤0.2% C. ≤0.2% D. ≤0.10% E. ≤0.10% | NMT 7% | 5-7 |
| Test result | initial | Disposable plastic device; white color; no visible damage | 1.69 mg/device (105.6%) | A. −0.29 B. ≤ND[2] C. ≤ND D. ≤ND E. ≤ND Unspecified impurities: BRL[1] Total Impurities: 0.3% | 5.3% | 6.2 |
| Test result | 1 | No change | 1.47 mg/device (91.9%) | A. −0.19% B. ≤ND C. ≤ BRL[1] D. ≤ND E. ≤ND Unspecified impurities: ND Total Impurities: 0.2% | 5.2% | 6.2 |
| Test result | 3 | No change | 1.36 mg/device (84.7%) | A. −0.21% B. ≤ND C. ≤ND D. ≤ND E. ≤ND | NA[2] | NA[2] |

TABLE 2-continued

| | | | | Stability data | | |
|---|---|---|---|---|---|---|
| Item | Testing interval, months | Appearance | Assay (HPLC) | Impurities/related substances | Water content | pH |
| | | | | Unspecified impurities: (RRT 1.4)- 0.05% (RRT 1.6)- 0.07% (RRT 2.9)- 0.09% Total Impurities: 0.42% | | |

[1]below reporting limit (0.05%)

[2]Not Detected

Conclusions: the powdered epinephrine formulation of the present invention showed good stability after 3 months at 40° C. and 75% relative humidity (RH). It contained 0.8% of the total impurities and similar assay of API. All results meet drug device combination products stability specifications.

Example 5: In Vivo Study of FMXIN002

In order to mimic PK achieved by intramuscular administration (IM) intranasal administration of epinephrine requires a higher dose. The clinical use of IN epinephrine in humans ranges from 1 mg up to 12 mg for different indications and in different formulations, with no serious adverse events (10). Prior studies using IN (intranasal) epinephrine showed 5 or 6 mg IN dose as equivalent to IM injection of 0.3 mg.

Based on clinical evidence, a starting IN dose of 1.6 mg is estimated to be equivalent to an IM dose of 0.1 mg. Hence a starting dose of IN epinephrine 1.6 mg represents a low dose that may be increased to 3.2 mg based on the safety and PK data. IN dose of 3.2 mg is estimated to be equivalent to IM dose of 0.2 mg, which is still below the range of approved IM dosage for anaphylaxis of 0.3-0.5 mg.

PK study is conducted in a stepwise manner with a starting lower dose, which may be increased if there are no serious adverse events (SAEs) and low exposure while constant and careful monitoring are maintained throughout the study by experienced clinical team including an allergy expert.

FMXIN002 is investigated in a single administration. The safety and tolerability of FMXIN002 can be based on the evidence from published literature and animal studies. Epinephrine for nasal administration (Adrenaline) is already approved for multiple administrations and available at higher doses as OTC product as well as for use in surgery. The safety of IN epinephrine in adults with seasonal allergies, has also been demonstrated in other studies where the administered dose of epinephrine was higher than the suggested dose in the current investigation of FMXIN002. In the study conducted by Chen et al. (9), the most common (≥5% overall) treatment-emergent adverse events (TEAEs) in the epinephrine nasal spray groups were nasal discomfort, tremor, headache, nasal congestion, rhinorrhea, dermatitis contact, and presyncope. In another clinical study of IN epinephrine in saline formulation in healthy adults, transient tremor was observed in one subject and palpitation in two subjects. Increase in heart rate, and diastolic and systolic blood pressures occurred at $T_{max}$. in most subjects but no correlation was found between these symptoms and the plasma concentrations of epinephrine. No serious adverse effects were observed in the subjects after IN epinephrine administration. Therefore, a good safety profile of FMXIN002 use is expected.

Comparative bioavailability between the test and reference products and also within treatment comparisons of the test product with and without allergen challenge will be determined by a statistical comparison of the $AUC_t$, $AUC_{inf}$ and $C_{max}$. parameters for epinephrine.

LIST OF REFERENCES

1. Reber, L. L., Hernandez, J. D., Galli, S. J. The pathophysiology of anaphylaxis. *J Allergy Clin Immunol.* 2017; 140(2): 335-348
2. Turner, P. J., Jerschow, E., Umasunthar, T., Lin, R., Campbell, D. E. and Boyle, R. J. Fatal Anaphylaxis: Mortality Rate and Risk Factors. *J Allergy Clin Immunol Pract.* 2017; 5(5): 1169-1178.
3. Kemp, S. F., Lockey, R. F., Simons, F. E. and World Allergy Organization ad hoc Committee on Epinephrine in, A. Epinephrine: the drug of choice for anaphylaxis—a statement of the world allergy organization. *World Allergy Organ J.* 2008; 1(7 Suppl): S18-26.
4. Sicherer, S. H. and Simons, F. E. R. Epinephrine for First-aid Management of Anaphylaxis. *Pediatrics.* 2017a; 139(3).
5. Sicherer, S. H., Simons, F. E. R., Section On, A. and Immunology. Epinephrine for First-aid Management of Anaphylaxis. *Pediatrics.* 2017b; 139(3).
6. Ring, J., Beyer, K., Biedermann, T., Bircher, A., Duda, D., Fischer, J., et al. Guideline for acute therapy and management of anaphylaxis; *Allergo J Int.* 2014; 23(3): 96-112.
7. Mylan Inc., *Highlights of Prescribing Information. EPIPEN®* (epinephrine injection, USP). USA: FDA; Revised: August, 2018. https://www.accessdata.fda.gov/scripts/cder/daf/. Accessed [Aug. 6, 2019].
8. Gold M S, Sainsbury R. First aid anaphylaxis management in children who were prescribed an epinephrine autoinjector device (EpiPen). *J Allergy Clin Immunol.* 2000;106:171-6
9. Chen, J., Yu, J., Chilampalli, C., DeCastrol, G., Narayanan, E., Wakaskar, R., et al. An Open-Label, 5-Treatment, Crossover, Single-Dose Pharmacokinetic Study of Epinephrine Nasal Spray in Comparison to EpiPen® Intramuscular Injection in Healthy Adults With Seasonal Allergies (abstract 434). AAAAI Annual Meeting. San Francisco, Caif., USA, INSYS Development Company, Inc. 2019

10. Cady R K, McAllister P J, Spierings E L, et al. A randomized, double-blind, placebo-controlled study of breath powered nasal delivery of sumatriptan powder (AVP-825) in the treatment of acute migraine (The TARGET Study). *Headache.* 2015;55(1):88-100. doi:10.1111/head.12472

11. Orgel H A, Meltzer E O, Bierman C W, Bronsky E, Connell J T, Lieberman P L, Nathan R, Pearlman D S, Pence H L, Slavin R G, et al. *J Allergy Clin Immunol.* 1991 Aug;88(2):257-64

12. Food and Drug Administration. FYs 2013-2017 Regulatory Science Report: Locally-Acting Orally Inhaled and Nasal Drug Products. OGD FY13-FY17 Regulatory Science Research Report—1; February 2018. https://www.fda.gov/drugs/generic-drugs/fys-2013-2017-regulatory-science-report-locally-acting-orally-inhaled-and-nasal-drug-products. Accessed [Nov. 20, 2019]

13. Nasal Spray and Inhalation Solution, Suspension, and Spray Drug Products—Chemistry, Manufacturing, and Controls Documentation; Guidance for Industry; CDER, July 2002

The invention claimed is:

1. A pharmaceutical composition comprising as an active agent an anti-anaphylactic adrenergic receptor agonist in the form of dry powder for intranasal administration, said composition comprising a first type of solid essentially spherical particles of a homogenous combination of said active agent in combination with at least one functional additive, and a second type of solid particles comprising a pharmaceutically acceptable carrier, wherein at least about 90% of said first type particles are of a mean particle size of about 10-30 microns and less than about 10% of said first type particles are of a mean particle size equal to or below about 10 microns and said second type particles are of a mean particle size of about 50-200 microns.

2. The pharmaceutical composition of claim 1, wherein said active agent is epinephrine or a pharmaceutically acceptable bitartrate, hydrochloride or borate salt thereof.

3. The pharmaceutical composition of claim 1, wherein said functional additive is sodium di-hydrogen phosphate.

4. The pharmaceutical composition of claim 1, wherein said carrier is any one of lactose monohydrate, lactose, a lactose functional analogue, or any mixture of at least two thereof.

5. The pharmaceutical composition of claim 1, wherein the first type particles and said second type particle are present at a weight ratio ranging from 1:9 to 9:1.

6. An epinephrine pharmaceutical composition in the form of dry powder for intranasal administration, comprising as active agent epinephrine bitartrate, said composition comprising a first type of solid spherical particles comprising epinephrine bitartrate in combination with sodium di-hydrogen phosphate, and a second type of irregular solid particles comprising lactose monohydrate as carrier, wherein said first type spherical particles have a narrow size distribution of 5-30 μm, and are dispersed between said irregular particles of lactose ranging between 40 μm to 240 μm, providing a metered therapeutically effective nominal dose of said epinephrine bitartrate.

7. The epinephrine pharmaceutical composition of claim 6, wherein the molar ratio between the epinephrine bitartrate to sodium dihydrogen phosphate is 0.9:1.

8. The epinephrine pharmaceutical composition of claim 6, wherein said therapeutically effective amount of epinephrine bitartrate is about 4.8 mg to 8 mg, equivalent to about 0.3 mg or 0.5 mg epinephrine administered intramuscularly (i.m.).

9. A disposable unit dosage form for intranasal administration to a subject of an epinephrine pharmaceutical composition according to claim 6, wherein said disposable unit dosage form is loaded with a predetermined single dose of the composition and provides the subject with a metered dose epinephrine bitartrate.

10. A disposable unit dosage form for intranasal administration to a subject of an epinephrine pharmaceutical composition according to claim 8, wherein said disposable unit dosage form is loaded with a predetermined single dose of the composition and provides the subject with a metered dose of about 4.8 mg to 8 mg epinephrine bitartrate being equivalent to about 0.3 mg or 0.5 mg epinephrine bitartrate administered intramuscularly (i.m.).

11. A method of treating anaphylactic shock in a patient in need thereof, said method comprising administering to said patient a therapeutically effective amount of a composition as defined in claim 1.

12. A method of treating anaphylactic shock in a patient in need thereof, said method comprising administering to said patient a therapeutically effective amount of an epinephrine composition as defined claim 8.

13. An epinephrine pharmaceutical composition in the form of dry powder for intranasal administration, comprising as active agent epinephrine bitartrate, said composition comprising a first type of solid spherical particles comprising epinephrine bitartrate in combination with sodium dihydrogen phosphate, and a second type of irregular solid particles comprising lactose monohydrate as carrier, wherein the size distribution of the first type of solid spherical particles as determined by Malvern Laser Diffraction instrument is D=21.4 μm, D (50)=82.0 μm and D (90)=133 μm, and wherein the amount of the obtained particles having the size less than 10 μm is about 3.7% v/v and of particles having the size of less than 5 μm is about 2.8% v/v, providing a metered therapeutically effective nominal dose of said epinephrine or pharmaceutically acceptable salt thereof.

* * * * *